United States Patent [19]
Klein et al.

[11] Patent Number: 5,632,993
[45] Date of Patent: May 27, 1997

[54] IMMUNOGENS AND THE USE THEREOF FOR OBTAINING ANTIBODIES AGAINST $HBA_{1C}$

[75] Inventors: Christian Klein, Weilheim; Christa Hübner-Parajsz; Hans-Georg Batz, both of Tutzing; Wolfgang Rollinger, Weilheim; Ulrich Essig, Planegg; Lorenz Kerscher, Penzberg, all of Germany

[73] Assignee: Boehringer Mannheim GmbH, Mannheim-Waldhof, Germany

[21] Appl. No.: 442,128

[22] Filed: May 16, 1995

Related U.S. Application Data

[62] Division of Ser. No. 290,342, Aug. 15, 1994, which is a continuation of Ser. No. 61,830, May 14, 1993, abandoned, which is a continuation of Ser. No. 873,663, Apr. 23, 1992, abandoned, which is a continuation of Ser. No. 304,808, Jan. 31, 1989, abandoned.

[30] Foreign Application Priority Data

Feb. 4, 1988 [DE] Germany .............. 38 03 330.5
Feb. 26, 1988 [DE] Germany .............. 38 06 198.8

[51] Int. Cl.$^6$ .............. A61K 39/385; A61K 38/14; C07K 14/805
[52] U.S. Cl. .............. 424/194.1; 424/193.1; 514/8; 514/18; 514/23; 530/300; 530/330; 530/385; 530/403
[58] Field of Search .............. 530/403, 395, 530/380, 385, 300, 330; 435/240.27; 424/184.1, 185.1, 193.1, 194.1; 514/8, 18, 23

[56] References Cited

U.S. PATENT DOCUMENTS

| | | | |
|---|---|---|---|
| 4,647,654 | 3/1987 | Knowles et al. | 530/326 |
| 4,727,036 | 2/1985 | Knowles et al. | 436/547 |
| 4,806,468 | 2/1989 | Wagner et al. | 435/7 |

FOREIGN PATENT DOCUMENTS

| | | | |
|---|---|---|---|
| 0185870 | 7/1986 | European Pat. Off. | G01N 33/68 |

OTHER PUBLICATIONS

The Merck Index, 9th edition, p. 463, "3475. Edestin", Merck and Co., Rahway, NJ 1976.

Primary Examiner—Thomas M. Cunningham
Attorney, Agent, or Firm—Felfe & Lynch

[57] ABSTRACT

The present invention provides immunogens for obtaining $HbA_{1c}$-specific antibodies, which immunogens have the general formula:

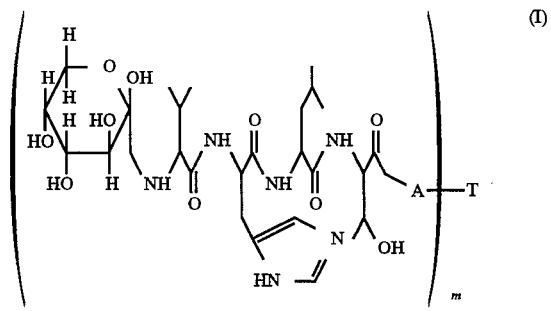

wherein $\underline{M}$ is 1 to 40, T is a carrier protein and A is a spacer which has a chain length of 10 to 20 atoms and has the general formula:

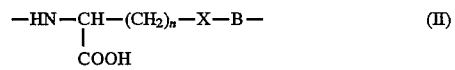

wherein X is a sulphur atom or au —NH— group, $\underline{n}$ is 1 to 4 and B is an organic radical which contains a succinimide group. The present invention also provides a process for obtaining antibodies which specifically bind glycosylated haemoglobin, wherein an immunogen of general formula (I) is injected into an organism capable of antibody formation and the antibodies are then obtained in known manner. These antibodies can be used for determining $HbA_{1c}$ in body fluids.

6 Claims, 3 Drawing Sheets

IMMUNOGENS AND THE USE THEREOF FOR OBTAINING ANTIBODIES AGAINST HBA$_{1C}$

This application is a divisional of copending application Ser. No. 08/290,342, filed Aug. 15, 1994, which is a continuation of application Ser. No. 08/061,830, filed May 14, 1993, and now abandoned, which is itself a continuation of application Ser. No. 07/873,663, filed Apr. 23, 1992, now abandoned, which is a continuation of Ser. No. 07/304,808, filed Jan. 31, 1989, now abandoned.

present invention is concerned with an immunogen for obtaining HbA$_{1c}$-specific antibodies, as well as a process for obtaining these antibodies.

Haemoglobin, which brings about the transport of inhaled oxygen and of carbon dioxide and is localised in the red blood cells, consists of four chains, of which, in each case, two have the same structure. It consists preponderantly of two α-chains and two β-chains. Haemoglobin is present in blood in an amount of more than 90% in this form, which is referred to as HbA$_0$.

Glycosylated haemoglobin is formed in vivo by the non-enzymatic reaction of haemoglobin with glucose. The glycosylation proceeds via the formation of a Schiffs base between the aldehyde group of the glucose and the amino group of the haemoglobin. The aldimine formed rearranges by an Amadori rearrangement to give the N-(1-desoxy-D-fructos-1-yl) radical. The glycosylated haemoglobin is stable in this rearranged form.

The glycosylated haemoglobins are designated with HbA$_1$ and the most important one of this group with HbA$_{1c}$. HbA$_{1c}$ is formed by the glycosylation of the free amino group of the valine residue which is present on the amino end of the β-chain of the haemoglobin. There is thereby formed an N-(1-desoxy-D-fructos-1-yl)-L-valine radical which, in the following, is referred to as "fructose valine".

The concentration of HbA$_{1c}$ in the blood is dependent upon the sugar concentration of the blood. In the case of adults, the proportion of HbA$_{1c}$ in the total haemoglobin is normally in the range of from 3 to 6%. In the case of an increased blood sugar level, the proportion of glycosylated haemoglobins in the total haemoglobin increases and can increase to 15%. Therefore, the determination of the proportion of HbA$_{1c}$ is a dependable parameter for monitoring the sugar metabolism. Since an erythrocyte and, with it, the stable HbA$_1$, achieves, on average, an age of 120 days, the determination of the proportion of glycosylated haemoglobins in the blood offers a good parameter for monitoring the carbohydrate metabolism, which is especially important in the case of diabetic patients. This parameter is independent of a brief increase of the blood sugar level after a carbohydrate-rich meal and serves, therefore, as a long-term parameter.

For the diagnosis of diabetes and for monitoring diabetic patients, it is, therefore, important specifically to determine the proportion of HbA$_{1c}$ in the blood.

There is a number of processes for the analysis of glycosylated haemoglobins. The most common methods depend upon the loss of positive charges in the haemoglobin molecule when the free amino groups of the β-chains-are reacted with glucose. In particular, column chromatographic and electrophoretic processes are used. Other methods attempt to determine colorimetrically the incorporated glucose molecules or the fructose molecules after the Amadori rearrangement (thiobarbituric acid method).

The previously known methods are, in part, very time consuming and laborious and, in part, ere not sufficiently specific for the glycosylated haemoglobin.

Therefore, there is a need for a simple process of determination which very specifically determines this glycosylated proportion of the total haemoglobin.

Such simple processes are the various variants of immunoassays which are known to the expert. In the case of homogeneous competitive immunoassays, for example, a labelled HbA$_{1c}$ derivative competes with HbA$_{1c}$ from the sample to be measured for the antibodies. As labelled HbA$_{1c}$ derivative there can be used a short synthetic peptide, which represents su epitope of the HbA$_{1c}$, which is bound to a label. In order now to be able to carry out the determination reproducibly with precise results, an antibody must be used which binds the labelled peptide and the HbA$_{1c}$ from the sample with substantially the same high affinity in order indeed to make possible a competitive reaction. Therefore, for carrying out the immunoassays, antibodies must be available which recognise HbA$_{1c}$ very specifically, i.e. specifically bind the glycosylated N-terminal end of the HbA$_{1c}$ β-chain but not bind the corresponding non-glycosylated N-terminal end of the HbA$_0$ β-chain.

A further variant of the competitive immunoassay is carried out in heterogenous phase. In this case, for example, a solid phase-bound synthesised peptide, which contains an HbA$_{1c}$ epitope, competes with the HbA$_{1c}$ from the sample for the specific antibody. The solid phase-bound peptide can be, for example, a conjugate of bovine serum albumin and a synthetic glycosylated peptide which has the sequence of an epitope of HbA$_{1c}$. For the carrying out of the variant, too, the antibody should bind the peptide and the HbA$_{1c}$ from the sample with substantially equally high affinity.

In order, now, to be able to carry out a sensitive and specific process for the detection of HbA$_{1c}$, it was important to obtain an antibody which specifically binds HbA$_{1c}$ but not HbA$_0$.

Processes for the detection of HbA$_{1c}$ are already known, as well as antibodies suitable for the process, for sample from published European Patent Application No. 0,185,870. However, all known antibodies suffer from the disadvantage that they show a very low affinity for the HbA$_{1c}$ molecule. Therefore, as a rule, before carrying out a determination, a denaturing must be carried out in order to liberate the antigenic determinants of the HbA$_1$ to such au extent that the antibodies can be bound to a sufficient extent. Such a process is laborious.

Furthermore, the immunogens used in the case of the process according to published European Patent Application No. 0,185,870 have the disadvantage that they bring about an immune response of only a low specificity. Thus, according to the process described therein, only polyclonal sheep and mouse sera could be obtained which have no measurable specificity with regard to the differentiation of HbA$_{1c}$ and HbA$_0$.

From published Federal Republic of Germany Patent Specification No. 34 39 610, a process is known for obtaining antibodies against HbA$_{1c}$ in which, as immunogen, there is used a conjugate of a sugar, a peptide residue of the β-chain of the haemoglobin and an immunogenic carrier. However, the antibodies obtained with this process do not show a sufficient selectivity and their relative affinity is low.

Therefore, it is an object of the present invention, starting from this prior art, to provide a process with which are formed highly specific polyclonal and monoclonal antibodies against HbA$_{1c}$ with high affinity.

A further object of the present invention is to provide antibodies which display molar relative affinities towards the native HbA$_{1c}$ molecule and a peptide which has the N-terminal sequence of the β-chain of the haemoglobin which differ by a factor which is as small as possible.

Thus, according to the present invention, there is provided an immunogen for obtaining $HbA_{1c}$-specific antibodies which immunogen has the general formula:

(I)

wherein $\underline{m}$ is 1 to 40, T is a carrier protein and A is s spacer with a chain length of 10 to 20 atoms which has the general formula:

(II)

wherein X is a sulphur atom or an —NH—group, $\underline{n}$ is 1 to 4 and B is sn organic radical which contains a succinimide group.

Surprisingly, we have found that in the case of the use of the immunogens according to the present invention, high specific antibodies can be obtained, the selectivity and affinity of which far exceeds those of the previously known $HbA_{1c}$ antibodies.

The immunogen according to the present invention consists of three parts, a hapten part which corresponds to the N-terminal end of the $HbA_{1c}$ protein, a spacer and an immunogenic protein. The hapten part of the immunogen according to the present invention contains the first 4 amino acids of the N-terminal end of the β-chain of the haemoglobin and, furthermore, a fructose molecule. As in the native $HbA_1$ protein, in the case of the immunogen according to the present invention, the amino acids valine, histidine, leucine and threonine are bound to the $C_1$ atom of the fructose molecule.

The preparation of the hapten part takes place in known manner. The solid phase synthesis (survey in G. Barany and R. W. Merrifield in Gross, Meienhofer, The Peptides, Vol. 2, pp. 3–285, New York, 1978) has proved to be especially suitable. For this purpose, the α-amino groups are advantageously protected with Nα-fluorenylmethoxycarbonyl radicals. The side chain functions are protected as tert.-butyl ether, tert.-butyl ester or as tert.-butoxycarbonyl radicals. In the case of the acidolytic splitting off of the finally synthesised peptide from the carrier, these protective groups are removed at the same time. The N-(1-desoxy-D-fructos-1-yl) radical is introduced in known manner by reaction of the peptide with glucose.

By subsequent Amadori rearrangement (cf. K. Heyns and H. Paulsen, J. Liebigs Ann. Chem., 627, 160–174 1959 and H. Röper et al., Carbohydrates, 116, 183–195/1983), there is obtained the desired N-(1-desoxy-D-fructos-1-yl)-peptide.

A further component of the immunogenic conjugate, which is important for the present invention, is the spacer which binds the hapten with the immunogenic protein. According to the invention, the spacer has a chain length of 10 to 20 atoms, whereby the chain can be formed from carbon, oxygen, nitrogen and/or sulphur atoms. For the chain length, only the chain-forming atoms are counted but not the hydrogen atoms or the side group atoms.

The spacer is bound to the carboxyl group of the threonine.

The spacer has the following general formula:

wherein X is a sulphur atom or an —NH— group and $\underline{n}$ is a whole number of from 1 to 4. Preferably, X is a sulphur atom and $\underline{n}$ is 1 or X is an —NH— group and $\underline{n}$ is 4.

The group B of the above general formula represents a known spacer molecule which contains a succinimidyl group. The construction of the group B is in itself not critical but it must have so many chain molecules that, together with the rest of the spacer part, it has a chain length of 10 to 20 atoms. A succinimidyl-hexanoyl radical is preferably used as group B.

The spacer is introduced in known manner. It contains an amino acid which can be bound precisely on the C-terminal end of the peptide and which carries an $NH_2$- or SH- group. The succinimidyl radical bringing about the binding with the carrier protein can be introduced via this amino or mercapto group. As amino acid, it is preferred to use cystein, homocystein, lysine or ornithine. If, as amino acid, the spacer contains cystein or homocystein, then there can first be used cystein or homocystein with a protected mercapto group, in which case a tert.-butylsulphenyl radical is preferably used as protective group, as starting amino acid for the solid phase synthesis of the peptide. Subsequently, the carrier protein is reacted with a bifunctional linker which provides the succinimidyl radical, for example maleimidohexanoyl-N-hydroxy-succinimide, and then the spacer-carrier protein conjugate is coupled to the liberated mercapto group of the cystein or homocystein. If, as amino acid, the spacer contains lysine or ornithine, then the amino acid with protected α-amino group is preferably first used as starting amino acid for the solid phase synthesis of the peptide, in which case, as protective group, there is preferably used a carbobenzoxy radical, and subsequently the liberated α-amino group of the peptide is reacted with the bifunctional linker. The peptide-amino acid-spacer conjugate is then coupled to the carrier protein, the binding taking place via the mercapto groups of the carrier protein.

As carrier protein, there can be used known proteins. Examples of appropriate proteins include albumins, such as bovine serum albumin and ovalbumin, haemocyanines, such as keyhole limpet haemocyanine, polyamino acids, such as poly-L-Lys and poly-L-(Lys:Glu) or enzymes, such as galactosidase. Edestin or galactosidase is preferably used as carrier protein.

Several hapten-spacer groups are preferably bound to the carrier protein. The number of bound groups depends upon the size of the carrier protein. As a rule, a maximum of 25% of the weight of the carrier protein can be bound to hapten-spacer groups. If edestin is used as protein, 10 to 50 hapten spacer groups are preferably bound.

With the immunogens provided by the present invention, there are obtained highly active, specific antibodies against $HbA_{1c}$. These antibodies display very little cross-reactivity with $HbA_0$.

The present invention also provides a process for obtaining antibodies directed against $HbA_{1c}$. For this purpose, an immunogen according to the present invention is injected several times into an appropriate organism and then the antibodies are obtained in known manner. For obtaining antibodies, as a rule mammals are immunised. Examples of appropriate mammals include mice, sheep, rabbits, rats and guinea pigs. The immunogen preferably dissolved in buffer and with the addition of a conventional adjuvant, for example Freund's adjuvant, is injected into the host animal. In order to achieve high antibody titres, the injection is repeated at regular intervals of time, for example every two to four weeks. The antisera which contain the polyclonal antibodies are obtained in the usual way from the blood of the host animals.

With the immunogens according to the present invention, there can also be obtained highly specific monoclonal antibodies with the use of the known hybridisation process of G. Köhler and C. Milstein, which is described, for example, in Nature, 266, 495/1977 and in Science, 208, 692 et seq./1980. For this purpose, after immunisation of the host organism, B-lymphocytes are isolated from the spleen of the immunised animal, fusioned with myeloma cells and the hybridoma cells formed are cloned. From the clones formed there are then isolated the cell lines which produce the antibodies which react specifically with $HbA_{1c}$ and show practically no cross-reaction with other molecules. The isolation of these cell lines is simple since a very high proportion of the clones produce specific antibodies. These cell lines are further cultured and the desired monoclonal antibodies cam then be obtained therefrom. The antibody activities are determined in known manner in the serum or in the hybridoma supernatants, usually with the use of an enzyme immunoassay.

The antibodies obtained according to the present invention are characterised by a high specificity and high affinity to $HbA_{1c}$. The cross-reaction with non-glycosylated haemoglobin and with other proteins present in body fluids is negligibly small. Therefore, they are outstanding appropriate for use in processes for the determination of $HbA_{1c}$ in body fluids. Especially appropriate monoclonal antibodies are MABs3.609.325, 3.51.56 and 3.230.140. The corresponding hybridoma cell lines have been deposited with the European Collection of Animal Cell Cultures, Porton Down, Great Britain, under the numbers 87120801, 88122302 and 88122301.

The following Examples are given for the purpose of illustrating the present invention, reference being made to the accompanying drawings, in which.

EXAMPLE 1.

The peptide fructose Val-His-Leu-Thr-Cys-OH was synthesised. The solid phase synthesis was carried out in a semi-automatic peptide synthesiser of the firm Labortec, Bubendorf, Switzerland.

The $F_moc$ group (fluorenylmethoxycarbonyl radical) was used as Nα-amino protective group. A description of this method of peptide synthesis is given by J. Meienhofer et al. in Int. J. Peptide Protein Res., 13, 35–42/1979.

The C-terminal Fmoc amino acid was coupled, as described by Meyerhofer, on to p-alkyloxybenzyl alcohol resin (firm Bachem, Bubendorf, Switzerland).

Synthesis protocoll for a synthesis cycle:

| step | time | reagent/solvent |
| --- | --- | --- |
| 1 | 2 × 1 min. | dimethylformamide (DMF) |
| 2 | 1 × 3 min. | piperidine/DMF 1:4 v/v |
| 3 | 1 × 7 min. | piperidine/DMF 1:4 v/v |
| 4 | 4 × 0.5 min. | DMF |
| 5 | 2 × 0.5 min. | isopropanol |
| 6 | stop | ninhydrin test |
| 7 | 2 × 1 min. | DMF |
| 8 | stop | addition of the next Fmoc amino acid and HOBt (1-hydroxybenzotriazole) in DMF |
| 9 | 2 min. | shaking |
| 10 | stop | addition of dicyclohexylcarbodiimide (DCC) in dichloromethane (DCM) |
| 11 | 90 min. | coupling |
| 12 | 3 × 1 min. | DMF |
| 13 | 2 × 1 min. | isopropanol |
| 14 | stop | ninhydrin test |

For the coupling according to steps 8 to 11, the $F_moc$ amino acids and DCC are, in each case, used in the threefold molar amount, referred to the loading of the starting resin. HOBt is used in a 4.5 fold molar amount.

After the coupling of the last N-terminal Fmoc amino acid, steps 1 to 5 of the synthesis cycle are passed through for splitting off the Fmoc protective group. Thereafter, the resin is shaken for 2 hours at ambient temperature in a 15 fold volume of dichloromethane (DCM)/trifluoroacetic acid (TFA)(1:1 v/v). After filtering, the resin is again washed twice with DCM/TFA (4:1 v/v), all the filtrates are combined and evaporated in a vacuum at 25° C. with the addition of toluene. The residue is mixed with diethyl ether. The solid material is filtered off and dried.

According to the above-described scheme, there is synthesised fructose-Val-His-Leu-Thr-Cys(StBu)OH. As starting resin, there are used 10 g. Fmoc Cys(StBu)-p-alkoxybenzyl alcohol resin loaded with 0.6 mMole/g. In the synthesis cycle, the following $F_moc$ amino acids are used successively:

1. 6.2 g. $F_moc$ Thr (tBu)
2. 6.4 g. $F_moc$ Leu
3. 11 g. $F_moc$ His (Trt)
4. 6.1 g. $F_moc$ Val.

The following abbreviations are used:

tBu; tertiary butyl ether

StBu: tertiary butyl thioether

OtBu: tertiary butyl ester

Trt: trityl

Z: benzyloxycarbonyl

—Cys(StBu): tertiary butyl sulphenylcystein.

The crude yield after splitting off of resin were 3.29 g. HVal-His-Leu-Thr-Cys (StBu)OH. TLC: (silica gel HPTLC Merck, elution agent: ethanol/glacial acetic acid/water 6:2:2 v/v/v) $R_f$=0.62. After spraying with 1% ninhydrin spray (Merck) and developing at 120° C. for 5 minutes, there was obtained red-violet coloration. In the case of spraying with a mixture of 200 ml. 0.4% methanolic resorcinol solution and 40 ml. 5N sulphuric acid (resorcinol sulphuric acid) and developing at 120° C. for 5 to 10 minutes, no coloration was obtained.

1 g. of the crude peptide was mixed with 540 mg. glucose and 50 ml. pyridine/glacial acetic acid and stirred for 5 days et ambient temperature. The reaction mixture was then evaporated in a vacuum at ambient temperature and subsequently the residue was taken up three times with 50 ml. of water and again evaporated to dryness. The residue was taken up in 50 ml. of water, applied to a column of Dowex 50 WX8 ($H^+$ form, 50×3.5 cm.) and washed with water until all of the glucose was eluted. Thereafter, the product was eluted with 1N ammonia and lyophilised. There were obtained 810 mg. of lyophilisate which were taken up in 0.1M triethylammonium acetate buffer (pH 8.5) and washed on a column of Affigel 601 (Biorad, 5×26 cm.) with 2 liters of 0.1M triethylammonium acetate buffer (pH 8.5) and thereafter with 2 liters of water. The product was then eluted with 0.1% formic acid and lyophilised. The lyophilisate this obtained was chromatographed on Polygosil C18, 5 μ(Macherey and Nagel) (gradient 0.1% TFA in water to 65% isopropanol in water, 0.1 TFA). There were obtained 283 mg. fructose Val-His-Leu-Thr-Cys (StBu)OH. TLC: (silica gel: elution agent as above): $R_f$=0.58. Coloration with ninhydrin: brownish. Coloration with resorcinol sulphuric acid: red-brown. Fab-MS (fast atom bombardment MS)(positive): $MH^+$=822.

For splitting off the cystein protective group, the above-obtained peptide was dissolved in 130 ml. 0.1M potassium phosphate buffer (pH 8.5), degassed several times and again aerated with nitrogen. The solution was then mixed with 778 mg. dithiothreitol and left to stand for 24 hours under nitrogen. Subsequently, it was acidified with hydrochloric acid to pH 5 and purified by chromatography on Polygosil C18 (gradient as above). There were obtained 178 mg. fructose Val-His-Leu-Thr-CysOH. FabMS; positive: $MH^+$= 734.

EXAMPLE 2.

The peptide fructose ValHisLeuThrLysOH was synthesised according to the synthesis scheme given in Example 1. As start resin, there were used 10 mg. Fmoc Lys(Z) p-alkoxybenzyl alcohol resin loaded with 0.48 mMole/g. The following Fmoc amino acids were used successively in the synthesis cycle:

1. 5 g. Fmoc Thr (tBu)
2. 5.1 g. $F_m$oc Leu
3. 8.9 g. $F_m$oc His (Trt)
4. 4.9 g. $F_m$oc Val.

Crude yield after splitting from the resin: 3.2 g. TLC: (silica gel HPTLC, elution agent see Example 1.3): $R_f$=0.58.

The crude peptide was stirred with 1.6 g. glucose at ambient temperature in 150 ml. pyridine/glacial acetic acid (1:1 v/v). The reaction solution was evaporated, the residue purified as described Example 1.3 on Dowex 50EX8$H^+$ and Affigel 601. There were obtained 1.7 g. fructose ValHisLeuThrLys(Z)OH. TLC: (silica gel HPTLC, elution agent see Example 1): $R_f$=0.58; coloration with sulphuric acid spray reagent: red-brown.

$^1$H-NMR (300 Mhz, $D_2O$): δ=0.85 (d, J=5.1 Hz, 3H,); 0.89 (d, J=4.9 Hz, 3H); 0.96 (d, J=7.1 Hz, 3H); 1.04 (d, J=6.8 Hz, 3H); 1.20 (d, J=1.20, 3H); 1.3–1.9 (m, 9H); 2.3 (m, 2H); 3.0–3.3 (m, 6H); 3.63–4.1 (m, 5H); 4.1–4.29 (m, 4H); 4.32 (d, J=5.4 Hz, 1H); 4.45 (m, 1H); 4.48 (m, 2H); 5.09 (s, 2H); 7.32 (s, 1H); 7.4 ("s", 5H); 8.63 ppm (s, 1H).

400 mg. of the above-obtained product were hydrogenated in 50 ml. methanol/water (5:1 v/v) with the use of palladium-active charcoal catalyst. The catalyst was filtered off, the filtrate evaporated and the residue chromatographed on Polygosil C18. Yield: 300 mg. TLC (silica Eel HPTLC, elution agent see Example 1): $R_f$=0.09; coloration with sulphuric acid spray reagent: red-brown).

EXAMPLE 3.

10 mg. Fructose ValHisLeuThrLysOH from Example 2 were taken up in 1 ml. 0.1M potassium phosphate buffer (pH 7). 6.2 mg Maleimidohexanoic acid N-hydroxysuccinimide ester in 2 ml. ethanol were added thereto. The reaction solution was stirred at ambient temperature for 14 hours and purified on Polygosil C18. After lyophilisation of the pure fractions, there were obtained 4.3 mg. fructose ValHisLeuThrLys(maleimidohexanoyl)OH. FAB-MS; positive: $MH^+$: 952.

$^1$H-NMR (300 MHz, DMSO ($D_6$)/$CD_3OD$): 0.83–1.06 (m, 12H; Leu-$CH_3$, Val—$CH_3$); 1.04 (d, J=6.5 Hz, 3H; Thr—$CH_3$); 2.01 (t, J=6.5 Hz, 2H; MH—CO—$\underline{CH_2}$) and 6.92 ppm (s, 2H; MH—CH=CH).

EXAMPLE 4.

5 g. Edestin from hemp seed (Roth) were stirred in 500 ml. 0.1M potassium phosphate buffer (pH 7.0) and mixed with a solution of 500 mg. maleimidohexanoic acid N-hydroxysuccinimide ester in 100 ml. ethanol. The solution was stirred for 90 minutes at ambient temperature, the solid material was filtered off with suction, washed twice with, in each case, 100 ml. of water, four times with, in each case, 100 ml. ethanol and again twice with, in each case 100 ml. of water. The solid material was slurried in 150 ml. of water and lyophilised. Yield: 4.34 g. Maleinimido groups/mole edestin: 17.

The number of maleinimido groups is determined as follows:

Solution A: 1 mM cystein, 0.5 mM EDTA in water

Solution B: 10 mM 5,5'-dithio-bis-(2-nitrobenzoate) (Ellmann's reagent) in 0.1M potassium phosphate buffer (pH 8.0)

Solution C: 1M Tris,HCl (pH 8.2)

8 mg. Meleimidohexanoyl-edestin are taken up in 39 ml. 0.05M potassium phosphate buffer and treated in an ultrasonic bath for 15 minutes. Thereafter, 1 ml. of Solution A is added thereto, followed by incubation for 10 minutes at 25° C. After stirring with 3.2 ml. of Solution C for 2 minutes at 25° C., 200 μl. of Solution B are added thereto, followed by incubation for 10 minutes at 37° C. The ample is then centrifuged for 15 minutes at 25° C. The extinction is measured in the supernatant at 405 nm. The blank value is obtained by proceeding analogously but with the use of the maleimidohexanoyl-edestin sample. The number of maleimido groups per nmole is given by:

$$\frac{\Delta E[mE] \times 43.4}{13.3}$$

wherein ΔE is the extinction difference between the blank value and the sample. The molar amount of edestin is obtained with the precisely weighed amount and the relative molecular weight of the edestin of 310,000:

$$\frac{mg. \text{ sample}}{0.31} = n\text{mole edestin}$$

250 mg. of the so obtained maleimidohexanoyl-edestin were mixed under an atmosphere of argon with 20 ml. 0.1M potassium phosphate buffer (pH 6.). 34 mg. fructose ValHisLeuThrCysOH, which has been obtained according to Example 1, were also added thereto with the exclusion of oxygen and the mixture stirred for 29 hours at ambient temperature. The solution was centrifuged, the precipitate washed three times with water and in each case again centrifuged. The solid residue was slurried in 10 ml. water and lyophilised. There were obtained 175 mg. of the conjugate of fructose ValHis LeuThrCysOH and maleimidohexanoyl-edestin, which is called immunogen 1.

The still free maleimido groups were determined as described above. From the difference to the original loading, it follows that the immunogen contains 14.6 mole peptide per mole of edestin.

EXAMPLE 5.

48 mg. β-galactosidase (EIA quality, Boehringer Mannheim GmbH) were dissolved under an atmosphere of argon in 2 ml. 0.1M potassium phosphate buffer (pH 7.0) gassed with argon. 5 mg. Fructose ValHisLeuThrLys(MH)OH, which had been obtained according to Example 3, were added thereto with the exclusion of oxygen and the mixture stirred at ambient temperature for 1 hour.

An AcA 202 column (23×24 cm.) was equilibrated with argon-saturated 0.9% aqueous sodium chloride solution. The total reaction solution was applied to this column. Elution was carried out with argon-saturated 0.9% sodium chloride solution and the protein fraction collected. 15 ml. immunogen solution were obtained (c=3.1 mg./ml.). The loading with immunogen can be determined by reaction of a sample with Ellmann's reagent: per mole of SH group, 1 mole carboxynitrothiopyridone is liberated ($\lambda_{max}$=412 nm., $\epsilon$=13,600 at pH 8.0).

β-Galactosidase of EIA quality contains 14 SH groups per molecule. After the reaction with the peptide, there are found 2 free SH groups, i.e. the loading is with 12 mole of peptide per mole of β-galactosidase.

The conjugate obtained from fructose ValHisLeuThrLys (MH)OH and βgalactosidase is called immunogen 2.

EXAMPLE 6.

For comparison, an immunogen was prepared with a comparatively long peptide chain. For this purpose, there was first prepared the peptide ValHisLeuThrProGluGluCysOH according to the synthesis scheme described in Example 1.

According to the synthesis scheme of Example 1 was prepared the peptide HValHisLeuThrProGluGluCys(StBu) OH. As start resin, there was used 10 g. of FmocCys(StBu) -E-alkoxybenzyl alcohol resin with a loading of 0.5 mMole/ g. The following amino acids were used in the synthesis cycle:

1. 6.4 g. $F_{m}$oc Glu (OtBu)
2. 6.4 g. $F_{m}$oc Glu (OtBu)
3. 5.1 g. $F_{m}$oc Pro
4. 6 g. $F_{m}$oc Thr (tBu)
5. 5.3 g. $F_{m}$oc Leu
6. 9.3 g. $F_{m}$oc His (Trt)
7. 5.1 g. $F_{m}$oc Val; the coupling was repeated once.

Crude yield after splitting off from the resin: 4.2 g. The crude product was chromatographed on Polygosil C18 as described in Example 1. The yield was 880 mg. HValHisLeuThrProGluGluCys(StBu)OH; TLC (silica gel, elution agent as in Example 1): $R_f$=0.53.

800 mg. of this peptide were then reacted with glucose as described in Example 1 and purified on Dowex 50WX8H$^+$ form end thereafter on Affigel 601. After chromatography on Polygosil C18, there were obtained 150 mg. of product. FabMS, positive: MH$^+$=1177. Analogously to Example 1, the cystein protective groups were then split off by the addition of dithiothreitol. There were obtained 78 mg. of fructose ValHisLeuThrProGluGluCysOH (FabMS positive: MH$^+$=1087. The peptide thus obtained was reacted with 322 mg. maleidohexanoyl-edestin as described in Example 4. There were thus obtained 200 mg. of immunogen which was used as comparative immunogen VI.

EXAMPLE 7.

As further comparative immunogen, there was prepared a conjugate of fructose ValHisLeuThrCys and pyridyldithiopropionyledestin. The peptide was prepared as described in Example 2.

For the preparation of the pyridyldithiopropionyledestin, 1 g. of edestin from hemp seed was taken up in 150 ml. 0.1M potassium phosphate buffer (pH 7.5). To this solution were added, with stirring, 10 mg. succinimidyl-3-(2-pyridyldithio)-propionate, dissolved in 12.5 ml. ethanol. The reaction mixture was stirred for 2 hours, the solid material then filtered off with suction, washed three times with, in each case, 100 ml. water, 100 ml. ethanol and again 100 ml. water. The solid material was taken up in 100 ml. water and lyophilised. 352 mg. of the pyridyldithiopropionyledestin thus obtained were mixed under an atmosphere of argon with 100 ml. 0.5M potassium phosphate buffer (pH 6.0). 49.5 mg. of the peptide fructose ValHisLeuThrCys were added thereto, also with the exclusion of oxygen, and the reaction mixture then stirred for 23 hours at ambient temperature. It was subsequently centrifuged, the precipitate was washed three times with, in each case, 50 ml. of water, twice with, in each case, 50 ml. ethanol and again once with water and, in each case, again centrifuged off. The solid residue was taken up in 50 ml. of water and lyophilised. For the determination of the loading, the liberated thiopyridone in the supernatant of the first centrifuging was measured. There were obtained 300 mg. of the conjugate of fructose ValHisLeuThrCys and pyridyldithiopropionyledestin as comparative immunogen called V2. The loading was 39 mole of peptide per mole of edestin.

EXAMPLE 8.

Polyhaptens were prepared for carrying out the screening test on anti-HbA$_{1c}$ antibodies. Polyhapten 1 was prepared from HValHisLeuThrProGluGluCysOH and pyridyldithiopropionyl-bovine serum albumin.

1 g. of bovine serum albumin was dissolved in 30 ml. 0.1M potassium phosphate buffer (pH 7.5). To this solution were added 226 mg. succinimidylpyridyldithio-propionate, dissolved in 15 ml. ethanol. The reaction mixture was stirred for 40 minutes at ambient temperature and the whole reaction solution chromatographed over ACA 202 (31×3 cm.); eluate 0.1M potassium phosphate buffer (pH 6.0). There were obtained 152 ml. of protein solution (c=6.6 mg./ml.). The solution was mixed with 280.5 mg. dithiothreitol and made up with 0.1M potassium phosphate buffer (pH 7.5) to 10 ml. Dilution was then carried out by the factor 6. The concentration of the liberated thiopyridone corresponded to the concentration of the dithiopyridyl groups used. From the extinction coefficient for thiopyridone at 340 nm of 8080 and the relative molecular weight of edestin of 310,000, there can be determined the loading: it is 36 mole/mole of protein.

10.5 ml. of the solution obtained of pyridyldithiopropionyl-bovine serum albumin and 47 mg. HValHisLeuThrProGluGluCysOH, which was obtained according to Example 6, was stirred for 1 day under argon (exclusion of oxygen). The loading was calculated by determination of the liberated thiopyridone at 33 mole peptide/ mole protein. Remaining reactive groups were saturated by the addition of 1.7 mg. cystein. The total reaction solution was chromatographed over an ACA 202 column (31×3 cm.), the protein fraction dialysed overnight against water and lyophilised. The product obtained is called polyhapten 1. Yield: 85 mg.

EXAMPLE 9.

For the preparation of polyhapten 2 (cf. Example 8), there were used 7 ml. pyridyldithiopropionyl-bovine serum albumin solution which was obtained in the manner described in Example 6. As peptide component, there were used 7.8 mg. of the peptide prepared according to Example 6 which carried a fructose on the amino acid Val. For this purpose, 800 mg. of the peptide HValHisLeuThrProGluGluCysOH obtained according to Example 6 were reacted as described in Example 1 with glucose and purified on Dowex 50 WX H-form and thereafter on Affigel 600. After chromatography on Polygosil C18, there were obtained 150 mg. of the glycosylated peptide; FabMS positive, MH$^+$=1177. After splitting off the cystein protective group with dithiothreitol, from 100 mg. of the glycosylated peptide there were obtained 78 mg. of the desired product; FabMS positive MH$^+$=1089. The product so obtained is called polyhapten 2.

Example 10.

In order to recognise the presence and specificity of antibodies against HbA$_{1c}$ in the sere of immunised mice or in the culture supernatant of the hybrid cells or in ascites, an Elisa process was used as test principle:

Microtiter plates were coated with 10 µg. of polyhapten 2 or 10 µg. polyhapten 1/ml. of coating buffer (0.2M sodium carbonate/bicarbonate; pH 9.5 to 9.5) at ambient temperature for 1 hour with shaking. After-treatment was then carried out for 10 minutes with 0.9% sodium chloride solution and 1% albumin solution. Subsequently, washing was carried out with 0.9% sodium chloride solution. Thereafter, incubation with 100 µl of sample was carried out at ambient temperature for about 1 hour and again washed with 0.9% sodium chloride solution. There followed a further incubation for 1 hour with 200 U/ml. of a sheep lab-anti-mouse Fcγ-peroxidase conjugate. After a further washing step with 0.9% sodium chloride solution, the peroxidase activity was determined in the usual way by reacting with ABTS for 15 minutes at ambient temperature. Thereafter, the extinction difference, mE difference, was determined at 405 nm.

The antisera which were obtained after immunisation with the immunogen 1 according to the present invention obtained according to Example 4 gave, in the case of all 100 immunised mice, a binding with polyhapten 2 and no or only weak binding with polyhapten 1. Thus, there were obtained antibodies binding selectively with polyhapten 2.

Of the antisera which were obtained after immunisation with the immunogen 2 according to the present invention prepared according to Example 6, 6 of 18 sera obtained from immunised mice reacted with polyhapten 2 and not with polyhapten 1. The binding to polyhapten 2 was thereby just as good as in t he case of immunogen 1. Thus, here, too, selective antibodies were obtained.

In the case of the immunisation carried out for comparison with the comparative immunogen V1, from 100 mice one antiserum was obtained which reacted only preferentially with polyhapten 2, all the other 99 antisera reacting equally well with both polyhaptens. Thus, in this case, it was not possible to obtained antibodies binding selectively with polyhapten 2.

In the case of immunisation with the comparative immunogen V2, no differentiating mouse antisera could be obtained. All antisera obtained from 100 mice reacted equally well with both polyhaptens. The binding to the polyhaptens was thereby weaker by a factor of 10 than in the case of the sera obtained with the immunogens 1 and 2 according to the invention.

EXAMPLE 11.

Balb/c and B10.D2 mice, 8 to 12 weeks old, were first immunised intraperitoneally (i.p.) with 100 µg. HbA$_{1c}$ (β1-4Cys, MHS)-edestin (immunogen 1) in complete Freund's adjuvant (CFA). After 6 and 10 weeks, two further immunisations were carried out. 100 µg. of immunogen in incomplete Freund's adjuvant (IFA) were thereby administered. 10 days after the last immunisation, the mice were bled in order to determine the antibody titre from the serum. 4 and 3 days before the fusion, the mice were again immunised intravenously with, in each case, 100 µg. immunogen in buffer.

For the fusion, with reference to Galfré, Methods in Enzymology, 73, 3/1981, $10^8$ cells of an immunised mouse were mixed with $2 \times 10^7$ myeloma cells (P3x63Ag8-653, ATCC-CRL 8375) and subsequently centrifuged for 10 minutes (300 g. 4° C.) The cells were again washed once with BSS (balanced salt solution) and centrifuged at 400 g in a 50 ml. pointed test tube. The supernatant was removed. The cell sediment was loosened and mixed with 1 ml. 60% PEG solution (MW 4000, Merck). After 1 minute in a waterbath, 5 ml. of RPMI 1640 medium (RPM=Rosewell Parker Memory Institute) without foetal calf serum (FCS) were added dropwise at ambient temperature over a period of time of 4 to 5 minutes, mixed up, made up with medium to 50 ml. and subsequently centrifuged for 10 minutes at 400 g. and 4° C. The sedimented cells were taken up in RPMI 16400 medium with 10% FCS. In each case, $10^5$ spleen cells were introduced into 24 well cell culture plates (firm Nunc). To each culture were added $5 \times 10^4$ peritoneal exudate cells as feed cells. On the following day, hypoxanthine-azaserine selection medium (100 mM hypoxanthine, 1 µg./ml azaserine) was added thereto.

After about 7 to 10 days, many clones were already visible. The supernatant of the primary cultures was tested according to an ELISA process described in Example 10. Primary cultures which showed no or only a smell cross-reaction with HbA$_0$ were further cloned with the help of a fluorescent-activating cell sorter (FACS) on 96 well cell culture plates (form Nunc). $1 \times 10^4$ peritoneal exudate cells serves as feed cells.

In this way, there could be isolated, for example, the hybridoma cell lines which have been deposited with the ECACC (European Collection of Animal Cell Cultures) under the deposit number 87120801, 88122301 and 88122302. The monoclonal antibodies MAB 3609325, MAB 3,230,140 and. MAB 3.51.56 can be obtained from this cell line.

For the production of ascites, mice were injected intraperitoneally with $5 \times 10^6$ hybrid cells, which had previously been pre-treated once or twice with 0.5 ml. pristane. 1 to 3 weeks thereafter, ascites fluid could be obtained from the mice with an IgG concentration of 5 to 20 mg./ml. The antibodies could be isolated therefrom in the usual was. These monoclonal antibodies are specifically directed against HbA$_{1c}$ and show no or only a slight cross-reactivity with HbA$_0$.

EXAMPLE 12.

| | Materials. |
|---|---|
| microtiter plates: | A: NUNC 4-42404 II<br>B: NUNC 2-69620 |
| 12 canal pipette: | Dynatech, catalogue No. 77-887-00 |
| plate shaker: | Flow Laboratories, Titertek, catalogue No. 77-471-00 |
| covering films: | Dynatech Plate Sealers, catalogue No. M 30 |
| ELISA reader: | Dynatech MR700 |
| coating buffer: | 50 mM sodium carbonate (pH 9.6) |
| sample buffer: | 10 mM sodium phosphate (pH 7.4), 0.9% sodium chloride, 0.1% Tween 20, 1% crotein C |
| wash buffer: | 0.9% sodium chloride, 0.1% Tween 20 |
| antibody-enzyme conjugate: | conjugate of peroxidase and the Fab fragment of a polyclonal antibody from sheep which is directed against the Fcγ part of mouse IgG, 25 mU/ml. in sample buffer |
| substrate: | 100 mmole/l. phosphate-citrate buffer (pH 4.4) 3.2 mmole/l. sodium perborate 1.9 mmole/l. ABTS (2,2'-azino-di-[3-ethylbenzthiazolin-6-sulphonic acid] diammonium salt) |
| antibody: | MAB 3.609.325 (ECACC 87120801) |
| polyhaptens: | polyhapten 1 according to Example 8<br>polyhapten 2 according to Example 9 |
| antigens: | HbA$_{1c}$ native<br>HbA$_0$ native |

In a preliminary experiment, there were determined the amounts of antibody to be used in the actual specificity experiments. For this purpose, microtitre plates were coated with polyhapten 1 or polyhapten 2. Per 100 μl. well, 1 μg. of polyhapten per ml. of coating buffer were incubated for 1 hour at ambient temperature. Thereafter, the solution was sucked out and washed three times with wash buffer.

Subsequently, to the solid phase-bound polyhapten were added dilution series of the antibody 3.609,325 (ascites), the dilution thereby taking place with sample buffer from 1:100 in the fourth stage. In each case, incubation was carried out with 100 μl./well for 1 hour at ambient temperature and subsequently washed.

After addition of a conjugate of peroxidase and the Fab fragment of a polyclonal antibody from sheep which is directed against the FCγ part of mouse IgG, the antibody bound to the hapten is determined via the reaction of the peroxidase with the added substrate. 100 μl. of conjugate/well are added and incubated for 1 hour at ambient temperature. The detection reaction is started by the addition of 100 μl of substrate/well into all of the wells. The measurement takes place in the ELISA reader at 405 nm (reference wavelength 490 nm).

As titre, there is defined that antibody dilution at which a half maximum binding takes place. This amount of antibody is used in the following experiment.

The specificity of the monoclonal antibodies was investigated. For this purpose, the reactivities of individual antibodies with different components present in solution were compared.

Into microtitre plates pre-coated with 1% crotein C were, in each case, pipetted 50 μl. of a solution of the monoclonal antibody in double titre concentration and 50 μl: of antigen solution (dilution series, see below), mixed and incubated for 30 minutes at ambient temperature. Thereafter, 100 μl. aliquots of the mixture were transferred into the microtitre plates coated with polyhapten.

| | |
|---|---|
| Dilution series:<br>fructose ValHisLeuThrCys(StBu)OH (according to Example 1<br>fructose ValHisLeuThrProGluGluCys (StBu)OH (according to Example 6)<br>fructose valine | from 5 μg./ml.<br>sample buffer with sample buffer in the fourth stage |
| HValHisLeuThrProGluGluCys(StBu)OH (according to Example 6)<br>HbA$_{1c}$<br>HbA$_0$ | from 100 μg./ml<br>sample buffer in fourth stage |

The concentration in mole/liter of a substance to be determined associated with the half-maximum binding is defined as molar relative affinity.

For the comparison of the reactivity of a monoclonal antibody with various components, the relative affinity of the monoclonal antibody for the component fructose ValHisLeuThrProGluGluCys(StBu)OH is taken as being equal to 100%. The reactivities, which are also referred to as cross-reactions, with other components are then given from the quotients of the relative affinities as follows:

cross-reaction =

$$\frac{C_{rel.aff.} \text{ fructose ValHisLeuThrProGluGluCys (StBu)}^{(nM)}}{C_{rel.aff.} X^{(nM)}} \times 100\%$$

The values obtained for the individual components are to be seen from the following Table 1.

Results were thereby also evaluated which were obtained with different antibodies obtained in an analogous manner.

Table 1 shows that with the immunogens according to the present invention, a plurality of monoclonal antibodies can be produced with bind HbA$_{1c}$ very specifically but not HbA$_0$. Compared with the antibodies which have been obtained with the use of the comparative immunogen V1 or with the antibodies known from published European Patent Specification No. 0,185,870, the antibodies obtained according to the present invention recognise HbA$_{1c}$ without special denaturing with substantially higher affinity. Therefore, they are very well suited for competitive immunoassays.

TABLE 1

Specificity investigation of <HbA$_{1c}$> clones
Results:

| reactivity with[+] | KMC19.2 | KMC19.3 | MAB 1 3.54.56 | MAB 2 3.230.140 | MAB 3 | MAB 4 | MAB 5 | MAB 3.609.3265 | MAB 6 | MAB 7 |
|---|---|---|---|---|---|---|---|---|---|---|
| polyhapten 2 | + | + | + | + | + | + | + | + | + | + |
| peptide A | 100 | 100 | 100 | 100 | 100 | 100 | 100 | 100 | 100 | 100 |
| HbA$_{1c}$ native | 4.4 | 9.4 | 15.3 | 20.0 / 22.0 | 20.7 | 40.4 | 25.0 | 40.0 | 4.1 | 7.1 |
| fructose-valine | <0.29 | <0.03 | <0.01 | n.d. | <0.56 | <0.11 | n.d. | n.d. | <0.04 | <0.1 |
| polyhapten 1 | – | – | – | n.d. | – | – | n.d. | n.d. | n.d. | n.d. |
| peptide B | <0.06 | <0.01 | <0.01 | <0.03 | <0.1 | <0.02 | <0.04 | <0.24 | 3 | 5.1 |
| HbA$_0$ native | <3.5 | <0.4 | <0.13 | <0.95 | <6.0 | <1.3 | <1.1 | <6.7 | <0.5 | <0.13 | n.d. = not determined
+ clone with the designation KMC: pub. Europ. Pat. Appln. No. 0,185,870
MAB 1 to MAB 5 and MAB 3.609,325: prepared with immunogen from Example 4
MAB 6 and MAB 7: prepared with comparative immunogen V1 from Example 6
peptide A: fructose ValHisLeuThrProGluGluCys(StBu)OH
peptide B: HValHisLeuThrProGluGluCys(StBu)OH

EXAMPLE 13.

As described in Example 12, into microtitre plates pre-coated with 1% crotein C are, in each case, pipetted in 50 μl. of a solution of MAB 3.609.325 in double titre concentration and 50 μl. HbA$_{1c}$ solution, mixed and incubated at ambient temperature for 30 minutes. Various concentrations of HbA$_{1c}$ are used.

Thereafter, 100 μL. aliquots of the mixtures are transferred into microtitre plates coated with polyhapten 2. The antibodies bound to the polyhapten 2 are, as described in Example 12, detected with the help of a conjugate of peroxidase and the Fab fragment of a polyclonal antibody from sheep which is directed against the Fcγ part of mouse IgG.

Figure 1:
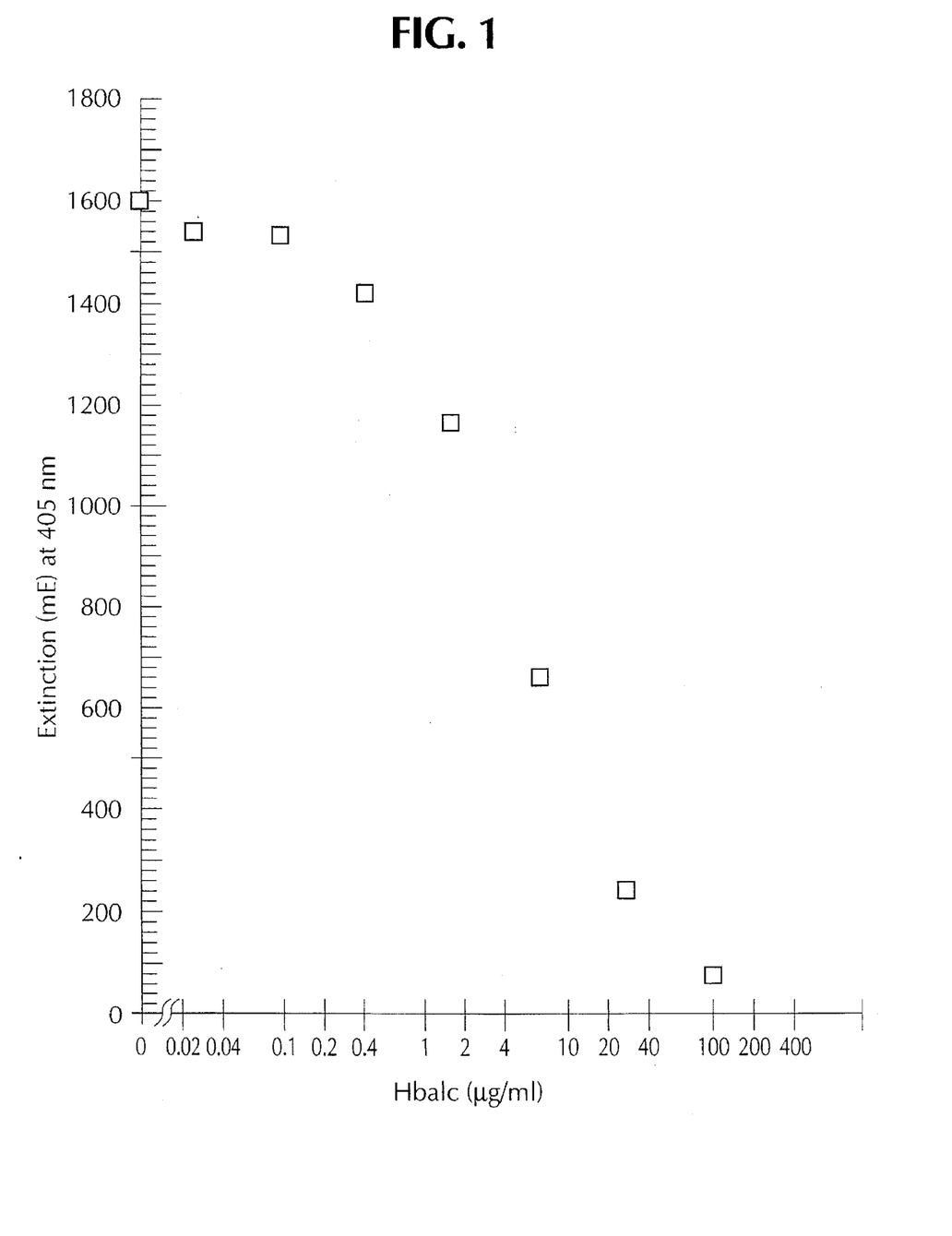
FIG. 1 shows a standard curve of the activity against $HbA_{1c}$ of monoclonal anti-$HbA_{1c}$ antibodies (MAB 3.509, 325)

The more HbA$_{1c}$ is present in the sample solution, the less antibodies bind to the polyhapten, i.e. the smaller is the measured extinction. In FIG. 1 of the accompanying drawings is illustrated the curve obtained in the case of the determination of HbA$_{1c}$.

EXAMPLE 14.

In each case, 10 sheep were immunised with immunogen 1 or 2 according to the present invention in complete Freund's adjuvant. In each case, the dosage amounted to 200 μg. of immunogen per animal for the first and each subsequent immunisation. The immunisations took place at monthly intervals.

The sera obtained were investigated for the presence and specificity of antibodies against HbA$_{1c}$ as described in Example 12. For this purpose, microtitre plates were coated with 0.04 μg./ml. of polyhapten 2. As antibody-enzyme conjugate there was used a conjugate of peroxidase and a rabbit anti-sheep immunoglobulin. The concentration used of this conjugate was 150 mU/ml. As antigens there were used HbA$_{1c}$ and HbA$_0$ native and as peptides HValHisLeuThrProGluGluCysOH and fructose ValHisLeuThrProGluGluCysOH.

The process was carried out in the manner described in Example 12.

The following samples were investigated:

Pool 1: mixture of aliquots of serum samples of all 10 animals which had been treated with the immunogen from Example 4 according to the present invention (blood sampling 45 days after first immunisation).

Pool 2: mixture of aliquots of serum samples of all 10 animals which had been treated with the immunogen from Example 5 according to the present invention (blood sampling 45 days after first immunisation).

Sample a: serum sample from sheep 3227 which had been treated with the immunogen from Example 4 according to the present invention (blood sampling 165 days after first immunisation).

Sample b: serum sample from sheep 3233 which had been treated with the immunogen from Example 4 according to the present invention (blood sampling 165 days after first immunisation).

Sample c: serum sample from sheep 3272 which had been treated with the immunogen from Example 5 according to the present invention (blood sampling 75 days after first immunisation).

The titre determination save the following results:

Pool 1: 1:5400

Pool 2: 1:8400

Sample a: 1:3700

Sample b: 1:3600

Sample c: 1:2600

Figure 2:
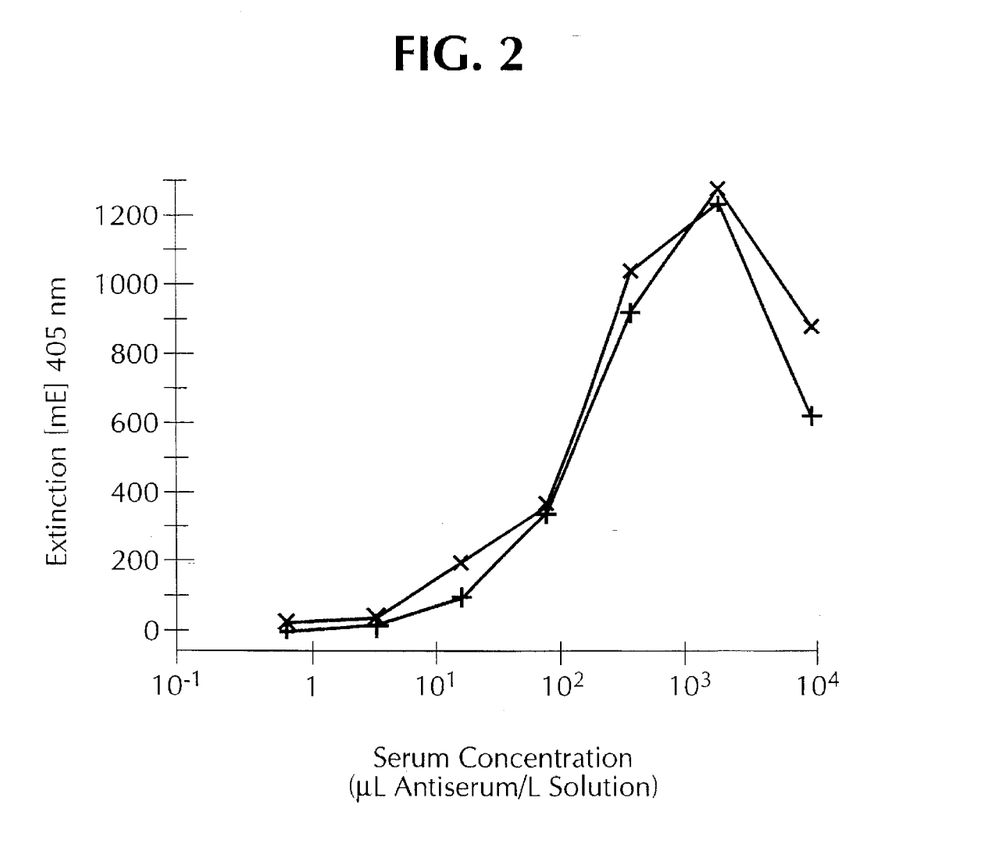
FIG. 2 shows the titre determination (double determination) for an antiserum obtained according to Example 14.

FIG. 2 of the accompanying drawings shows an Example for the course of the extinction depending upon the antiserum concentration.

EXAMPLE 15.

Figure 3:
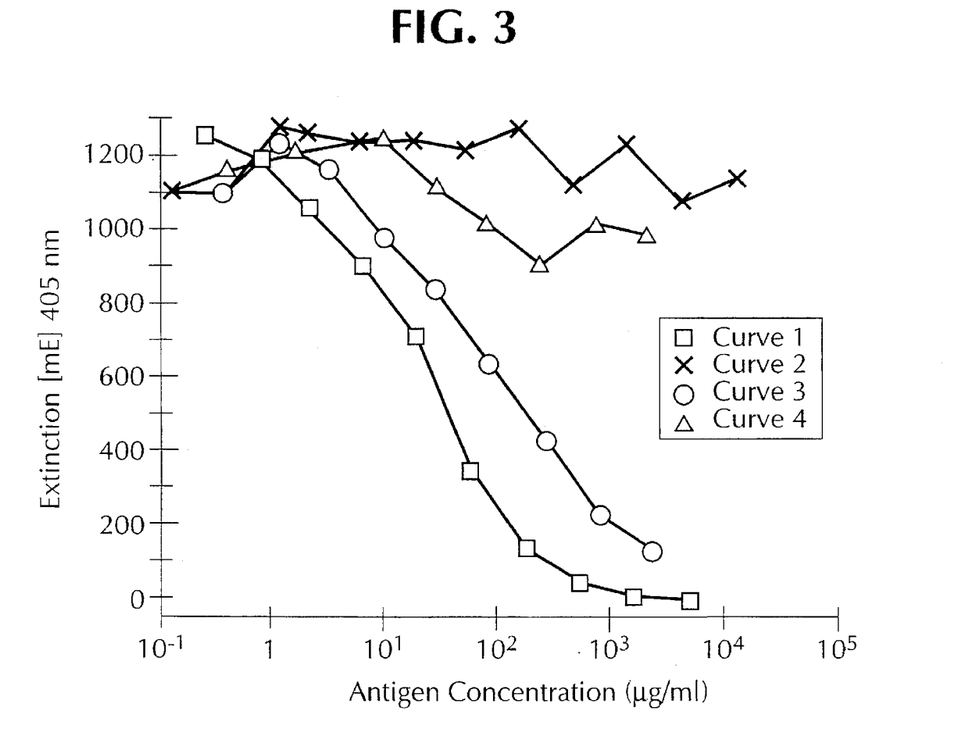
FIG. 3 shows a diagram with the relative affinities of the antibodies towards peptides and haemoglobin.

In the manner described in Example 14, the affinities and specificities of antibodies to glycosylated and non-glycosylated antigens were determined. The results are given in the following Tables 2 and 3, as well as in FIG. 3 of the accompanying drawings. In FIG. 3:

| curve | antigen | maximum concentration used (nmole/l.) |
|---|---|---|
| 1 | peptide A | 5340 |
| 2 | peptide B | 16000 |
| 3 | HbA$_{1c}$ | 2670 |
| 4 | HbA$_0$ | 2670 |

The Tables show that, with the immunogens according to the present invention, there can be produced highly specific polyclonal antibodies which bind very specifically HbA$_{1c}$ but not Hb$_0$. It is also shown that the polyclonal anitbodies recognised HbA$_{1c}$, without denaturing, with high affinity.

Furthermore, from the results of the various pools, which represent a mixture of the polyclonal antibodies obtained from, in each case, 10 sheep after treatment with immunogens according to the present invention, it can be seen that, in the case of the use of the immunogens according to the present invention, a very high percentage of the immunised animals produce suitable antibodies.

TABLE 2

Affinity of the antibodies to glycosylated and non-glycosylated antigens relative affinity (nmole/l.)

| sample | peptide A[+] | peptide B[++] | $HbA_{1c}$ | $HbA_0$ | cross-reaction $HbA_0/HbA_{1c}$ |
|---|---|---|---|---|---|
| Pool 1 | 21 | >>16000 | 30 | >>2670 | <<1.1% |
| Sample a | 33 | >>16000 | 115 | >>2670 | <<4.3% |
| Pool 2 | 15 | >>16000 | 18 | >>2670 | <<0.7% |
| sample c | 21 | >>16000 | 134 | >>2670 | <<5.0% |

[+]peptide A: fructose ValHisLeuThrProGluGluCys(StBu)OH
[++]peptide B: HValHisLeuThrProGluGluCys(StBu)OH

TABLE 3

Specificity investigations of polyclonal antibodies against $HbA_{1c}$
Results:

| reactivity with[+] | pool 1 | sample a | pool a | sample c |
|---|---|---|---|---|
| polyhepten 2 | + | + | + | + |
| peptide A | 100 | 100 | 100 | 100 |
| $HbA_{1c}$ native | 70 | 28.6 | 83.3 | 15.7 |
| peptide B | <<0.13 | <<0.2 | <<0.09 | <<0.13 |
| $HbA_0$ native | <<0.8 | <<1.2 | <<0.5 | <<0.8 |

[+]Pool 1. sample a: prepared from immunogen 1 of Example 4
Pool 2, sample c: prepared from immunogen 2 of Example 5

We claim:

1. Immunogen of formula:

(Fructose-Val-His-Leu-Thr-A)$_m$-T wherein m is a number from 1 to 40;

A is a spacer molecule which has a chain length of from 10 to 20 atoms and is of formula:

—HN—CH—(CH$_2$)$_n$—X—B
        |
        COOH wherein

X is a sulfur atom or an amide group, n is a whole number from 1 to 4,

B comprises a succinimide group, and;

T is a carrier protein.

2. The immunogen of claim 1, wherein B has a chain length of 12–18 atoms.

3. The immunogen of claim 1, wherein m is a number from 3–20.

4. A conjugate of fructose-Val-His-Leu-Thr-CysOH and maleimidohexanoyl-edestin.

5. The immunogen of claim 1, wherein Xaa is Cys.

6. The immunogen of claim 1, wherein Xaa is Lys.

* * * * *